United States Patent [19]

Cynshi et al.

[11] Patent Number: 4,732,889

[45] Date of Patent: Mar. 22, 1988

[54] PHARMACEUTICAL COMPOSITION FOR THE TREATMENT OF THE ANEMIA OF RHEUMATOID ARTHRITIS

[75] Inventors: Osamu Cynshi, Tokyo; Koji Mizuno, Saitama, both of Japan

[73] Assignee: Chugai Seiyaku Kabushiki Kaisha, Tokyo, Japan

[21] Appl. No.: 825,222

[22] Filed: Feb. 3, 1986

[30] Foreign Application Priority Data

Feb. 6, 1985 [JP] Japan ................................. 60-21165

[51] Int. Cl.$^4$ .............................................. A61K 37/10
[52] U.S. Cl. ....................................... 514/8; 514/814; 514/825
[58] Field of Search ...................... 424/99; 514/8, 814, 514/825

[56] References Cited

U.S. PATENT DOCUMENTS 4,254,095 3/1981 Fisher et al. .......................... 424/1.1
4,303,650 12/1981 Takezawa ............................. 424/99

FOREIGN PATENT DOCUMENTS

148605A2 2/1984 European Pat. Off. .
2467214 4/1981 France ................................. 424/99
2501692 9/1982 France ................................. 424/99
2135676A 2/1984 United Kingdom .

OTHER PUBLICATIONS

Merck Index, 10th Edition, p. 533, No. 3632.
Chem. Abst., 93:161360c, 1980.
Merle et al., Clin. Pharmacul. Ther., 28:216–222, 1980.
Fisher, "Kidney Hormones", Erythropoietin, pp. 551–569, 19.

*Primary Examiner*—J. R. Brown
*Assistant Examiner*—John W. Rollins, Jr.
*Attorney, Agent, or Firm*—Morgan & Finnegan

[57] ABSTRACT

A pharmaceutical composition for the treatment of the anemia of rheumatoid arthritis comprising a therapeutically effective amount of human erythropoietin (EPO) in a parenterally acceptable vehicle is disclosed. Human EPO may be extracted from human urine or also be prepared by expressing in a host cell the gene coding for the amino acid sequence of human EPO.

1 Claim, No Drawings

PHARMACEUTICAL COMPOSITION FOR THE TREATMENT OF THE ANEMIA OF RHEUMATOID ARTHRITIS

The present invention relates to a pharmaceutical composition for the treatment of the anemia of rheumatoid arthritis that comprises a therapeutically effective amount of human erythropoietin (hereinafter referred to as "human EPO") in a parenterally acceptable vehicle.

The term "human EPO" as used hereinafter means a polypeptide having the amino acid sequence inherent in human beings, with or without sugar chains. Examples of the human EPO include one that is derived from human urine (hereinafter referred to as "human urinary EPO"), one obtained by expressing in a host cell the gene coding for the amino acid sequence of human EPO (this type of human EPO is hereinafter referred to as "human rEPO"), one obtained from a tissue culture of human kidney cancer cells, and one obtained by cultivating a hybridoma resulting from cell fusion of a human cell line having the ability to produce human EPO. The term "erythropoietin"(hereinafter referred to as "EPO") will mean a trace physiologically active substance that acts on erythroblastic stem cells present not only in humans but also in other animals so as to accelerate the differentiation of such stems cells into mature erythrocytic cells, and proliferation of the latter. While numerous studies on human urinary EPO have been reported, the pharmaceutical utility of human EPO still remains unknown in many respects.

High incidence of anemia as one of the complications in patients with rheumatoid arthritis has been known for many years (see, for example, Nilsson, F., Acta. Med. Scand. Suppl., 210, 193 (1948), and Roberts, F. D. et al.; Blood, 21, 470 (1983)); and severe anemia associated with rheumatoid arthritis is of particular clinical concern in the treatment of the disease.

Many hypotheses have been proposed for explaining the mechanism behind the development of anemia, and they include the blockade of iron in the reticuloendothelial system due to abnormal iron metabolism, impaired iron release, spleen involvement, impaired EPO production, hemolysis, and disorders in hemopoietic stem cells. The anemia of rheumatoid arthritis is believed to develop as a result of iron deficiency in red blood cells due to abnormal iron metabolism because most causes of the anemia in rheumatoid arthritis are of the type of normocytic hypochromemia, the average erythrocyte hemoglobin levels are decreased, the number of erythroblasts in bone marrow are decreased, and the amount of free protoporphyrin in erythrocytes are increased (see, for example, Wintrobe M. M.; Clinical Hematology, 671, Lea & Febiger, London (1974)). However, some researchers reported that there was no correlation between the increase in the plasma EPO levels in patients with rhematoid arthritis and the degree of anemia (see, for example, Ward, H. P. et al., J. Lab. Clin. Med., 74, 93 (1969); and Pavlovic-Kentera, v. et al, Scand. J. Haematol., 23, 141 (1979)). This observation suggests that impaired EPO production may also be involved in the anemia of rheumatoid arthritis. However, in the absence of any observation demonstrating that patients with rheumatoid arthritis suffer from disorders in the kidney, thyroid body or other EPO producing tissues, it is yet to be established that impaired EPO production actually accompanies rheumatoid arthritis.

Other causes that have been proposed for explaining the fact that the plasma EPO levels in patients with rheumatoid arthritis are not increased include bone marrow hyporesponsiveness to EPO and the possibility of production of an EPO inhibitor. It has, therefore, been very doubtful that administration of human EPO to patients with the anemia of rheumatoid arthritis is effective for the purpose of treating the disease. As already mentioned, numerous papers exist that report the various functions of human urinary EPO but nobody has demonstrated by in vivo experimentation with humans or animals that human urinary EPO and other types of human EPO are effective as therapeutic agents for the treatment of anemia associated with rheumatoid arthritis.

The present inventors prepared a highly pure form of human urinary EPO and they also obtained human rEPO by expressing in a host cell the gene coding for the amino acid sequence of human EPO. Using these two types of human EPO, the inventors studied their therapeutic effects for anemia in animal models suffering from rheumatoid arthritis diseases. To their great surprise, these types of human EPO turned very effective against the anemia, and therefore, the inventors concluded that they are useful as therapeutic agents for the treatment of anemia of rheumatoid arthritis. The present invention has been accomplished on the basis of this finding.

The principal object, therefore, of the present invention is to provide a novel pharmaceutical composition for the treatment of anemia of rheumatoid arthritis that comprises a therapeutically effective amount of human EPO in a parenterally acceptable vehicle.

The types of human EPO that are incorporated in the composition of the present invention as the active ingredient may be prepared by a variety of means. For example, human urinary EPO may be extracted from normal human urine or the urine of patients with hypoplastic anemia (T. Miyake et al., J. B. C., 252, 5558 (1977); and J. P. Lewin et al., J. Lab. Clin. Med., 66, 987 (1965)). Human rEPO may be prepared by genetic engineering procedures comprising obtaining a messenger RNA (mRNA) corresponding to the amino acid sequence of human EPO, preparing a recombinant DNA using the mRNA, and expressing the DNA gene in a suitable host cell such as a bacterium (e.g. E. coli), a yeast, or a plant or animal cell line (see, for example, Sylvia, L. H., Proc. Natl. Acad. Sci., U.S.A., 81, 2708 (1984)). While various animal cell lines are available as host cells, cultured cell lines derived from humans or mammalian animals are preferred and they include COS cells, Chinese hamster ovary (CHO) cells, and mouse C-127 cells. Human EPO may also be prepared from, for example, tissue cultures of human kidney cancer cells (Unexamined Published Japanese Patent Application Ser. No. 55790/1979), from human lymphoblastic cells having the human EPO producing ability (Unexamined Published Japanese Patent Application Ser. No. 40411/1982), and from a culture of the hybridoma obtained by cell fusion of a human cell line. Any of the types of human EPO that are prepared by these methods are useful in the present invention so long as they enable the proliferation of mature red blood cells having sufficient oxygen transport to be useful in the treatment of anemia of rheumatoid arthritis.

The human EPO present in the urine or the supernatant of culture obtained by the aforementioned methods may be further concentrated and purified by routine isolation and purification procedures such as, for example, precipitation with an organic solvent (e.g. benzoic acid, ethanol, acetone or tannic acid), salting out with ammonium sulfate, etc., dialysis by, for example, vacuum concentration, chromatographic techniques (e.g. gel permeation chromatography, ion-exchange chromatography and affinity chromatography), and electrophoretic techniques (e.g. isoelectric electrophoresis and gel electrophoresis). These isolation and purification procedures may be employed either independently or in combination.

The human EPO thus prepared may be stored either frozen or in a dehydrated state attained by freeze-drying, vacuum drying or other suitable methods. Alternatively, an aqueous solution containing the human EPO may be mixed with a water-soluble salt or a hydrophilic organic solvent to precipitate the active ingredient, which then is dehydrated for storage purposes. If desired, the human EPO may be dissolved in a suitable buffer solution and aseptically filtered such as through a Millipore filter to prepare an injection.

The pharmaceutical composition of the present invention for the treatment of anemia of rheumatoid arthritis may be mixed with conventional anemia treating agents such as chalybeates, vitamin $B_{12}$ and androgens, either in a dosage form or just before use. Illustrative chalybeates include dried ferrous sulfate, iron fumarate, iron dextran, iron gluconate, iron glucuronate and iron orotate.

The dosage and frequency of administration of the human EPO incorporated in the therapeutic composition of the present invention may be determined depending upon the condition of the patient under therapeutic regimen. In ordinary cases, a preparation containing 0.1–500 μg, preferably 5–100 μg of human EPO may be administered to an adult in 1–7 doses for one week, assuming a human erythropoietin activity of $9 \times 10^4$ units per mg.

The pharmaceutical composition of the present invention for the treatment of anemia of rheumatoid arthritis may contain a stabilizer selected from among polyethylene glycol, proteins, sugars, amino acids, inorganic salts, organic salts and sulfur-containing reducing agents. These stabilizers may be employed either individually or in combination. They are preferably incorporated in the composition of the present invention in an amount ranging from 0.11 to 10,000 parts by weight per part by weight of human EPO. If two or more stabilizers are used, it suffices that the total of their amounts is within the range specified above. These stabilizers are used in the form of an aqueous solution containing a corresponding amount of a specific stabilizer to provide the appropriate concentration and pH. This aqueous solution is adjusted to have an osmotic pressure ratio of 0.1–3.0, preferably 0.8–1.2. The pH of the aqueous solution is adjusted to a value between 5.0 and 9.0, preferably between 6 and 8.

The composition of the present invention may be prepared in a dosage form in the presence of an adsorption preventing agent.

Reference Example 1: Preparation of human urinary EPO Step (1): Partial purification from human urine Urine from patients with hypoplastic anemia was subjected to the procedures of T. Miyake et al. (J. B. C., 52, 5558 (1977)); viz., (1) deionization on a Sephadex G50 column, (2) adsorption on DEAE-cellulose in a batch system, (3) precipitation with ethanol, and (4) chromatography on a DEAE-agarose column. By these procedures, a partially purified form of human urinary EPO was obtained.

Step (2): Reverse phase chromatography

The partially purified human urinary EPO was dissolved in a 0.1% trifluoroacetic acid (Aldrich Chemical Co., Inc.) solution containing 24% propanol (Wako Pure Chemical Industries, Ltd.) and the solution was subjected to purification by HPLC with Hitachi Model 638-50. Absorption in the ultraviolet range at 280 nm and 220 nm was used as an indicator.

The so prepared sample was loaded onto a YMC-C8 column (6 mm × 30 cm, product of Yamamura Chemical Co., Ltd.) equilibrated with a 0.1% trifluoroacetic acid solution containing 24% n-propanol, and the column was eluted with the same equilibrating solution. After the unadsorbed fractions were eluted, the concentration of n-propanol was increased to 26% for eluting the active fractions. The fractions containing the EPO activity were collected and concentrated to a volume of 0.1–0.2 ml by ultrafiltration using Centricon-100 (trade name of Amicon).

Step (3): High-performance molecular sieve chromatography

The concentrated sample was loaded onto a TSK-G300 SW column (7.8 mm × 60 cm, product of Toyo Soda Manufacturing Co., Ltd.) equilibrated with a 0.1% TFA solution containing 26% n-propanol, and the column was eluted with the same equilibrating solution. Peaks having the EPO activity were obtained at positions corresponding to molecular weights of 25,000–30,000. These active fractions were collected and freeze-dried. The fractions had a specific activity of about $9 \times 10^4$ units/mg.

The specific activities of the samples prepared in the respective steps (1) to (3) are listed in Table I.

TABLE I

| Step | Specific activity (U/mg) |
| --- | --- |
| (1) partial purification | 600 |
| (2) reverse phase chromatography | 10,000 |
| (3) high-performance molecular sieve chromatography | 90,000 |

Assay method: In accordance with the method of N. N. Iscove et al., J. Cell. Physiol., 83, 309 (1974).

Reference Example 2: Preparation of human rEPO derived from CHO cells

A plasmid incorporating the gene coding for the amino acid sequence of human EPO was expressed in Chinese hamster ovary cells (CHO cells) to produce human rEPO. The procedures employed are specifically described in Japanese Patent Application Ser. No. 281862/1984 (filed Dec. 27, 1984), entitled "Vector harboring accessory DNA for the transformation of eucaryotic cells". A summary of the procedures is given below.

The DNA from a lambda HEPOFL 13 clone incorporating the gene coding for the amino acid sequence of human EPO derived from fetal human liver cells was digested with EcoRI, and the recovered small EcoRI fragment harboring the gene coding for the amino acid sequence of human EPO was inserted into the EcoRI site of plasmid RKI-4. The plasmid then was incorporated into DHFR-deficient CHO cells so as to transform them. The transformed CHO cells were cultured in an alpha-medium deficient of nucleic acids. Cells harboring at least one DHFR gene were selected and employed in the production of human rEPO, with the concentration of methotrexate in the medium being increased incrementally. The human rEPO in the supernatant of the finally obtained culture had an activity of 20 units/ml.

The CHO cells were cultivated in a serum-free liquid culture medium for 3 days and pure human rEPO was isolated by the procedures employed in the preparation of pure human urinary EPO. The so obtained human rEPO was found to have an activity of 6,600 units/ml as measured by the method of Krystal et al. (J. Lab. Clin. Med., 97, 144 (1981)). SDSpolyacrylamide gel electrophoresis showed that this human rEPO was comprised of a single protein band. The human rEPO was mixed with 0.1% BSA and dialyzed against physiological saline to prepare samples for use in subsequent experiments.

Experiments: Therapeutic effects of human rEPO for the treatment of anemia in adjuvant-initiated arthritis rats 1. Preparation of adjuvant-induced arthritis rats To the tails of 8-week-old female LEW/Crj rats (bought from Japan Charles River Co., Ltd.), 0.05 ml of an adjuvant (50 mg/ml of strain Aoyama B) was administered subcutaneously. At 27 days of injection, the development of arthritis was confirmed in the adjuvant-treated rats, which then were subjected to the measurement of the following erythrocyte parameters.

Parameters (1) Hemoglobin: Blood samples withdrawn from the eye were subjected to spectrophotometry on RaBA Super sold from Chugai Pharmaceutical Co., Ltd.
(2) Hematocrit: Blood samples were withdrawn from the eye through a hematocrit tube and the hematocrit was measured by routine procedures.
(3) Erythrocyte count: Blood samples withdrawn from the eye were diluted with ISOTON (trade name of Coulter Electronics, Inc.) and erythrocyte counting was performed with a Coulter counter Model ZBI.

The erythrocyte parameters in the adjuvant-treated rats as compared with the normal values are summarized in Table II.

TABLE II

| Parameter | Normal rats | Treated rats |
|---|---|---|
| Hematocrit (%) | 46.4 ± 0.74 | 41.9 ± 0.46** |
| Hemoglobin (g/dl) | 14.9 ± 0.27 | 12.2 ± 0.40** |
| Erythrocyte count ($\times 10^4/mm^3$) | 860 ± 7 | 736 ± 10** |

**$P < 0.01$ (Assayed at 27 days of adjuvant sensitization each group consisting of 4 rats)

As Table II shows, all of the erythrocyte parameters in the adjuvant-treated rats differed significantly from those in the normal rats, and the rats were found to be in the anemic state.

2. Therapeutic effects of human urinary EPO for the treatment of anemia in the adjuvant-treated rats Each of the adjuvant-treated rats prepared in 1 was injected intraperitoneally with human urinary EPO (25 units/rat/day) for seven consecutive days starting at 18 days of adjuvant treatment. The treated groups were compared with the control group for the erythrocyte parameters as shown in Table III.

TABLE III

| Parameters | Control | EPO treated rats |
|---|---|---|
| Hematocrit (%) | 43.2 ± 0.51 | 51.1 ± 0.54** |
| Hemoglobin (g/dl) | 11.8 ± 0.27 | 14.4 ± 0.40** |
| Erythrocyte count ($\times 10^4/mm^3$) | 705 ± 18.6 | 829 ± 20.0** |

**$P < 0.01$ (Seven rats per group)

3. Therapeutic effects of CHO cell derived human rEPO for the treatment of anemia in adjuvant-treated rats Each of the adjuvant-treated rats prepared in 1 was injected intraperitoneally with CHO cell derived human rEPO (10 units/rat/day) for seven consecutive days starting at 18 days of adjuvant treatment. The treated groups were compared with the control group for the erythrocyte parameters and the results are shown in Table IV.

TABLE IV

| Parameters | Control | EPO treated rats |
|---|---|---|
| Hematocrit (%) | 41.9 ± 0.28 | 46.8 ± 0.53** |
| Hemoglobin (g/dl) | 11.9 ± 0.33 | 14.7 ± 0.16** |
| Erythrocyte count ($\times 10^4/mm^3$) | 715 ± 6.7 | 837 ± 17.0** |

**$P < 0.01$ (Seven rats per group)

As Table III and IV show, all of the erythrocyte parameters in the group of rats treated With human EPO were significantly improved as compared with the control group. It is therefore concluded that the human EPO prepared in accordance with the present invention is effective for the treatment of anemia associated with rheumatoid arthritis. The two types of human EPO had no toxicity under the experimental conditions used.

The following examples are provided for the purpose of further illustrating the present invention but are by no means taken as limiting.

EXAMPLE 1

A solution was aseptically prepared from the formulation indicated below.

| Ingredients | Amount (parts by weight) |
|---|---|
| CHO cell derived human rEPO | 1 |
| Human serum albumin | 100 |
| Distilled water for injection | to make 100,000 |

The solution was distributed among vials and freeze-dried, followed by the sealing of the vials.

EXAMPLE 2

Freeze-dried preparations were made as in Example 1 except that the human serum albumin was replaced by 100 parts by weight of dextran 40.

EXAMPLE 3

An aqueous solution containing mannitol (5 g), human urinary EPO (1 mg), human serum albumin (100 mg), sodium acetyltryptophan (2.154 mg) and sodium caprylate (1.33 mg) in 100 ml was prepared aseptically.

Small portions (1 ml) of the solution were put into vials and freeze-dried, followed by the sealing of the vials.

EXAMPLE 4

An aqueous solution containing human urinary EPO (1 mg), polyethylene glycol 4000 (500 mg), ethylene oxidepropylene oxide copolymer (30 mg) and sodium chloride (800 mg) in 100 ml of a 0.05 M phosphate buffer solution (pH 7.0) was prepared aseptically. Small portions (1 ml) of the solution were put into ampules, which then were sealed by fusion.

EXAMPLE 5

An aqueous solution containing CHO cell derived human rEPO (0.5 mg), glycine (1 g) and sorbitol (1 g) in 50 ml of a 0.05 M phosphate buffer solution (pH 7.0) was prepared aseptically. Small portions (0.5 ml) of the solution were put into vials and freeze-dried, followed by the sealing of the vials. A 0.1% aqueous solution of methyl cellulose was also prepared aseptically and 1-ml portions of the solution were put into ampules for making solubilizing media.

EXAMPLE 6

An aqueous solution containing human urinary EPO (1 mg), human serum albumin (50 mg) and mannitol (500 mg) in 100 ml was prepared aseptically. Small portions (1 ml) of the solution were put into vials and freeze-dried, followed by the sealing of the vials. An aqueous solution containing ferric gluconate (3 g) and NaCl (2.7 g) in 300 ml was also prepared aseptically, and 3-ml portions of this solution were put into ampules which then were sealed by fusion. The content of one vial was transferred into one ampule and a complete solution was obtained by thorough mixing. The solution was injected intravenously over time (2-3 minutes).

What is claimed is:

1. A method for treating the anemia of rheumatoid arthritis in a patient who is suffering from anemia of rheumatoid arthritis which comprises administering to said patient a therapeutically effective amount of human erythropoietin for treating anemia of rheumatoid arthritis in a pharmaceutically acceptable carrier.

* * * * *